United States Patent [19]
Liao et al.

[11] Patent Number: 5,505,831
[45] Date of Patent: Apr. 9, 1996

[54] CONCENTRATION OF BIOLOGICAL SAMPLES ON A MICROLITER SCALE AND ANALYSIS BY CAPILLARY ELECTROPHORESIS

[75] Inventors: Jia-li Liao; Stellan Hjerten, both of Uppsala, Sweden; Christopher Siebert, Berkeley, Calif.

[73] Assignee: Bio-Rad Laboratories, Inc., Hercules, Calif.

[21] Appl. No.: 11,485

[22] Filed: Jan. 26, 1993

[51] Int. Cl.⁶ .................................. B01D 57/02
[52] U.S. Cl. .................................. 204/451
[58] Field of Search ............................. 204/182.8, 180.1, 204/183.2

[56] References Cited

U.S. PATENT DOCUMENTS 5,110,434  5/1992  Zhu et al. ............................ 204/183.2

Primary Examiner—John Niebling
Assistant Examiner—C. Delacroix-Muirheid
Attorney, Agent, or Firm—Townsend and Townsend and Crew

[57] ABSTRACT

The present invention provides new methods for the concentration of ionic solutes, particularly ampholytes, such as, for example, peptides, proteins and nucleic acids. The methods are based on the fact that the electrophoretic migration velocities of solutes decrease upon a decrease in the absolute value of the zeta-potential of a solute or the pore size of the electrophoresis medium, and upon an increase in the cross-section of the electrophoresis chamber, the viscosity of the electrophoresis medium, or the electrical conductivity of the electrophoresis medium. When applied to capillary electrophoresis, the methods described herein permit concentration of a solution of solutes in the same capillary tube as is used for the electrophoretic analysis. Alternatively, however, the sample can be withdrawn from the capillary tube following concentration of the solution of solutes and processed by techniques other than high-performance capillary electrophoresis (HPCE).

3 Claims, 1 Drawing Sheet

CONCENTRATION OF BIOLOGICAL SAMPLES ON A MICROLITER SCALE AND ANALYSIS BY CAPILLARY ELECTROPHORESIS

FIELD OF THE INVENTION

This invention relates to methods for the concentration of dilute biological mixtures, particularly mixtures of peptides, proteins and nucleic acids. Following concentration, the biological mixture can be analyzed by high performance capillary electrophoresis or by other techniques known to those skilled in the art.

BACKGROUND OF THE INVENTION

Capillary electrophoresis is a technique of considerable interest in the analysis of biological mixtures as it provides a number of distinct advantages over other separation processes. One advantage of capillary electrophoresis is the small volume of the capillary tube interior. This permits one to perform separations on extremely small volumes, and at high speeds. Another advantage of capillary electrophoresis is the rapid rate at which heat is dissipated outward from the capillary tube due to the capillary's narrow bore. This permits the use of a high voltage to drive the electrophoresis which, in turn, provides for separations at high speed and with high efficiency. Each of these advantages renders capillary electrophoresis particularly useful for analyzing samples of biological interest, particularly mixtures of peptides, proteins, and nucleic acids.

One of the problems with capillary electrophoresis, however, is that frequently the sample to be analyzed is very dilute. As with other methods of analysis, there is a detection limit under which one cannot go if accurate analytical data are required. A concentration step, therefore, is often required prior to starting the method of analysis. Frequently, however, this concentration step cannot be carried out without a large loss of sample, particularly when the same volume is 1–10 µL or smaller. Accordingly, there is a need for efficient concentration techniques which are applicable to small-volume samples. Additionally, there is a need for concentration techniques which can be used in free electrophoresis for high-mobility proteins and peptides. These and other problems are addressed by the present invention.

SUMMARY OF THE INVENTION

New methods have now been developed for the concentration of ionic solutes, particularly ampholytes, such as, for example, peptides, proteins and nucleic acids. These methods are applicable to both small-volume samples and large-volume samples. The methods of the present invention are based on the fact that an electrophoretically migrating zone can be concentrated if the front of the migrating zone can be forced to move more slowly than the rear of the migrating zone. The electrophoretic velocity, v, of a solute is determined by the expression:

$$v = u \frac{I}{q \times \kappa} \quad (I)$$

Where the mobility, u, can be calculated from the equation $$u = \frac{\epsilon \times \zeta}{4\pi\eta} \quad (II)$$

(where I is equal to the current, q is equal to the cross-sectional area of the electrophoresis chamber, $\kappa$ is equal to the electrical conductivity, $\epsilon$ is equal to the dielectric constant, $\zeta$ is equal to the potential of the solute and $\eta$ is equal to the viscosity.)

According to Equations I and II, the front of an electrophoretically migrating zone can be forced to move more slowly than its rear if the zone is permitted to migrate toward a section of the electrophoresis chamber where u decreases and/or q, $\kappa$, or $\eta$ increase. Therefore, by decreasing the absolute value of the zeta-potential of a solute or the pore size of the electrophoresis medium, by increasing the cross-section of the electrophoresis chamber, the viscosity of the electrophoresis medium, the electrical conductivity of the electrophoresis medium or the opposing flow rate, the electrophoretic migration velocities of the solutes can be decreased and the sample can be concentrated. The present invention provides different methods wherein these parameters are manipulated to obtain a concentrated, narrow zone of solutes.

In practice, the whole electrophoresis tube is filled with a solution of solutes to be concentrated. When a voltage is applied between the anolyte and the catholyte, the solutes start migrating, but they cease moving as they approach the end of the tube provided that the above parameters have been given appropriate values in this part of the tube. Using the methods of the present invention, a sample can be concentrated into a zone having a width from about 0.2 mm to about 0.5 mm. Accordingly, for a tube length of 200 mm this width corresponds to a 400–1000 fold concentration. The concentrated zone of solutes can be withdrawn from the tube and subjected to further studies and analysis. Alternatively, the concentrated zone can be used as a starting zone for an in-tube electrophoresis upon a reversal of the polarity of the electrodes. The tendency of the very narrow starting zone to broaden during the initial phase of the electrophoresis step, i.e., the mobilization stage, can be counteracted by a step involving displacement electrophoresis, electrophoresis in a steep pH gradient, or on-tube dialysis against a diluted buffer.

Other advantages, features and embodiments of the present invention will become apparent from the detailed description which follows.

BRIEF DESCRIPTION OF THE DRAWINGS

FIG. 2 depicts the electopherogram obtained following free zone electrophoresis of a dilute sample of model proteins (A), and of the same solute sample concentrated in-tube by isoelectric focusing toward a steep, non-buffering pH gradient (B). The width of the applied sample zone in (A) was 3–4 mm and in (B), it was 130 mm (i.e., the length of the capillary tube).

FIG. 3 depicts the electopherogram obtained following free zone electrophoresis of a dilute sample of model proteins (A), and of the same sample concentrated on-tube by zone electrophoresis toward a small-pore gel (B). The width of the applied sample zone in (A) was 3–4 mm and in (B), it was 140 mm (i.e., the length of the capillary tube).

FIG. 4 depicts an electrophoresis or capillary tube having attached directly to it a dialysis tubing formed by dipping the tube three times in a 3% nitrocellulose (collodion) solution and subsequently, manually breaking the wall of the electrophoresis tube to create pores through which the current can pass. The glass pieces are held together by the collodion membrane formed.

FIG. 5 represents approaches used to concentrate a dilute sample solution. These approaches include displacement electrophoresis in a dilute buffer in combination with a hydrodynamic counterflow (A); and zone electrophoresis in a dilute buffer in combination with a hydrodynamic counterflow (B). The counterflow velocity is equal and opposite to the electrophoretic velocity.

FIG. 6 depicts the device used in a method for off-tube concentration and desalting of a sample of solutes (A). Once the sample is added, the salts will be removed from the sample by diffusion (B) and the sample will be concentrated by the Donnan effect and also by the fact that the small-pore gel is semi-dry and, therefore, will readily absorb water (C).

FIG. 7 depicts the electopherogram obtained following zone electrophoresis of a dilute sample of model proteins (A), of the same solute sample off-tube concentration and desalting of the dilute sample (B).

FIG. 8 depicts an apparatus used for the off-tube concentration and desalting of a sample solution of solutes. The sample to be concentrated and desalted is added to a vial having contained therein a semi-dry small-pore gel. Once the sample is added, the salts will be removed from the sample by diffusion and the sample will be concentrated by the Donnan effect and also by the fact that the small-pore gel is semi-dry and, therefore, will readily absorb water.

DETAILED DESCRIPTION OF THE INVENTION AND PREFERRED EMBODIMENTS

Figure 1A:
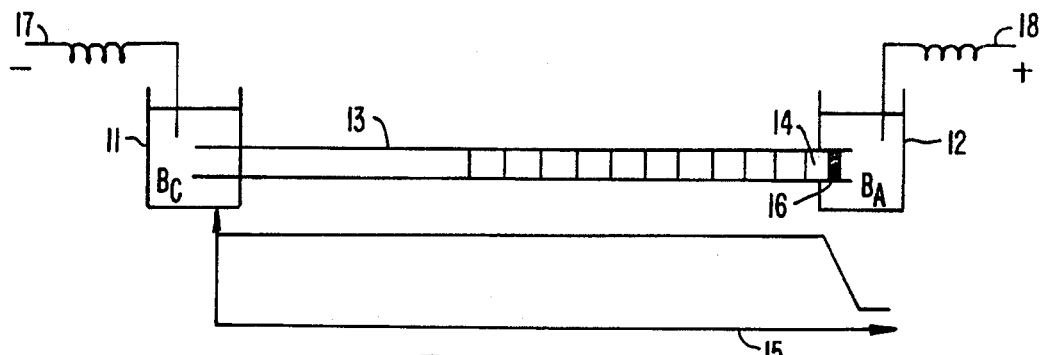
FIG. 1 represents various approaches used to concentrate a dilute sample solution. These include isoelectric focusing in a pH gradient (A); zone electrophoresis toward a small-pore gel (B); zone electrophoresis toward a gradient in effective cross-section (C); and zone electrophoresis toward a gradient in electrical conductivity (D). It should be noted that during the mobilization and electrophoretic analysis, the polarity of the electrodes is reversed, i.e., the anode is to the left and the cathode is to the right.

In one aspect of the present invention a method is provided for the concentration of a solution of solutes, the method comprising: (a) filling a capillary tube with a solution of solutes, the capillary tube having a first end in contact with an anolyte and a second end in contact with a catholyte, the catholyte differing in pH from the anolyte by a pH differential; and (b) applying a voltage between the anolyte and the catholyte of sufficient intensity to cause the solutes to migrate elecrophoretically to the first end of said capillary tube, while (c) imposing a means of concentrating the solutes at the first end of the capillary tube.

The concentration method of the present invention can be used to concentrate ionic polymers or weak electrolytes, preferably ampholytes (e.g., peptides, proteins and nucleic acids), or compounds which can be transformed into these classes of substances by complex formation. When the sample is in the form of a powder, it is dissolved in the buffer to be used in the subsequent zone electrophoresis or, in the leading buffer, if the electrophoretic analysis is to be performed by displacement electrophoresis. When the sample is a solution, for instance, a biological sample, it can often be added directly to the capillary or electrophoresis tube, provided that the pH is such that the solutes migrate electrophoretically in the desired direction. The pH of the sample should therefore be measured when the solutes are weak acids, weak bases or ampholytes, or when the solutes contain residues of such substances. A pH adjustment may be necessary. When the sample has a very low ionic strength, a small volume of a concentrated solution of the electrophoresis buffer should be added. When the pH and the background electrolyte of the sample disturb the concentration and electrophoresis steps, the solution of solutes should be dialyzed (i.e., desalted) by micro methods, as will be described herein. These methods can be used for macromolecules and are based on dialysis in polyacrylamide gels or in dialysis tubing having extremely small pores.

In the methods of the present invention, the sample to be concentrated can be added directly to the capillary tube. Alternatively the sample can be continually electrophoresed into the tube. In this method, for example, the capillary tube is filled with a buffer containing no sample. The sample is introduced into the catholyte. Upon applying a voltage between the anolyte and the catholyte, the sample which is present in the catholyte is introduced into the capillary tube wherein it is concentrated using one of the methods of the present invention.

The capillary tubes used in the methods of the present invention are conventional capillary tubes. The size of the capillary tube in terms of both length and internal diameter is not critical to the invention. Thin-walled, thin diameter tubes are preferred. Also preferred are fused silica capillaries. The inner walls of the capillary tube may be treated with a monolayer of a polymer, examples of which include linear polyacrylamide, dextran and methyl cellulose, to eliminate zone distortion due to electroendosmosis and the adsorption of solutes by the capillary tube wall. The treatment agent may be deposited by conventional methods well known in the art of manufacturing capillaries.

For electrophoretic concentration and separation, the voltage used is not critical to the invention, and may vary widely. Typical voltages range from about 500 V to about 30,000 V, preferably from about 1,000 V to about 10,000 V.

In one aspect of the above concentration method, step (c) comprises creating a steep pH gradient 14 at the first end of the capillary tube 13 through the use of an anolyte having a pH which is substantially different from both the pH of the catholyte and the pH of the solution of solutes to be concentrated.

In this concentration method, for example, the cathode vessel 11 is filled with a buffer, $B_C$, having a high pH (such as, for example, 0.01M Tris-HCl, pH 8.5) and the anode vessel 12 is filled with a buffer, $B_A$, having a low pH (such as, for example, 0.5M Tris HCl, pH 2.5). The entire capillary tube 13 is filled with the sample solution dissolved in the same buffer as that used in the cathode vessel (i.e., 0.01M Tris-HCl, pH 8.5). Due to the difference in pH between the cathode 17 and the anode 18 and sample solution, a steep pH gradient 14 is immediately created at the anodic end of the capillary tube 13 when the voltage is switched on, and localized within a relatively short distance inside the capillary tube 13 from that end. (The graph in FIG. 1(A) 15 depicts the steep pH gradient 14 that is created when the voltage is switched on.) At the same time, the anions present in the sample begin to migrate toward the anode 18 (See, e.g., FIG. 1(A)). The strong anions pass through the steep pH gradient 14, while the ampholytes remain in the steep gradient regions and concentrate into very narrow zones 16. In addition to concentrating the sample, this concentration step offers the further advantage of desalting the sample from strong electrolytes. The weak electrolytes, such as, for example, carboxylic acids, will also concentrate in the pH gradient. The weak electrolytes are noncharged at low pH, whereas the ampholytes are positively charged at low pH. The diffusional broadening of weak electrolytes, therefore, is not counteracted by the zone sharpening (i.e., "backward migration") typical of ampholytes.

When the concentration of the solution of solutes is performed by means of an anolyte having a low pH, the number of protons, $N_{H+}$, entering the capillary per time unit is of interest since it determines the position and the progress of the pH gradient in the capillary tube. This number is governed by the following expression:

$$N_{H+}=V_{H+} \times q \times n_{H+} \qquad (III)$$

where $V_{H+}$ is equal to the migration velocity of the protons in the anolyte, q is equal to the cross-sectional area of the capillary, and $n_{H+}$ is equal to the number of protons per volume unit in the anolyte.

$$\text{Since } v_{H+} = E \times U_{H+} = \frac{I}{q \times \kappa} \times U_{H+}$$

(where E is equal to the field strength in the capillary, $U_{H+}$ is equal to the mobility of the proton in the anolyte, I is equal to the current, and κ is equal to the electrical conductivity), Equation III can be rewritten as:

$$N_{H+} = \frac{I \times U_{H+} \times n_{H+}}{\kappa} \qquad (IV)$$

The conductivity, κ, is determined by the expression:

$$\kappa = \Sigma c_i \times u_i \qquad (V)$$

where $c_i$ is the concentration of ion i in coul/mL. For example, in the 0.5M Tris-HCl solution of pH 2.5 (i.e., the stop solution) used as an example in the above description, it is seen that $$\kappa=(C_{H+} \times U_{H+})+(C_{Tris} \times U_{Tris})+(C_{OH-} \times U_{OH-})+(C_{Cl-} \times U_{Cl-}) \qquad (VI)$$

The pH of the stop solution (and accordingly, $C_{H+}$) should be at least one pH unit below the pI-value of the solute in the sample having the lowest pI-value. The third term in Equation (VI) can be neglected since $C_{OH-}$ is very small at low pH-values. The remaining second and fourth terms in Equation (VI) can, accordingly, be used to manipulate the conductivity, i.e., the Tris-HCl buffer solution used in the anode vessel should be adjusted to a molarity which gives the solution a proper conductivity.

According to Equations (IV) and (VI), when the molarity decreases, the number of protons entering the capillary increases. At an excessively low molarity, the pH gradient in the capillary tube will, therefore, migrate toward the cathode during the concentration step. In contrast, at a very high molarity, none or only a small change in the pH of the capillary tube will occur and thus, the solutes will migrate out of the capillary tube. It has been determined that the molarity of the stop solution should be such that a virtually stationary pH gradient is created at a distance of about 0.5 mm to about 3 mm from the end of the capillary, thereby preventing the concentrated solute zone from migrating out of the capillary tube. The suitable molarity of the stop solution can readily be established experimentally by those skilled in the art through the use of colored solutes and transparent glass capillary tubes.

The above explanations and descriptions are directed to the presence of anions in the solution of solutes to be concentrated. However, it will be readily apparent to those skilled in the art that cations present in the sample to be concentrated can be treated in an analogous way.

Figure 1B:
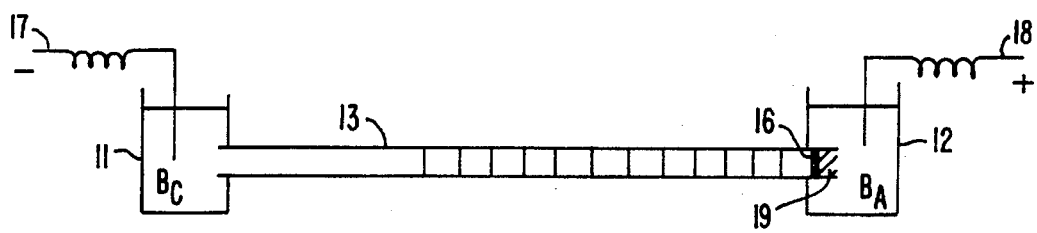

In another aspect of the above method for concentrating a solution of solutes, step (e) comprises introducing into the first end of the capillary tube 13 a short plug of a small-pore gel 19 such that upon applying the voltage between the anolyte 12 and the catholyte 11, the solutes cease migrating for stearic reasons when the solutes come into contact with the small-pore gel, thereby concentrating into very narrow zones 16. (See, e.g., FIG. 1(B).)

In this method, the gel is prepared in a glass tube with an inside diameter of about 1 mm. The pores of the gel must be small enough such that the solutes cannot penetrate the gel. Any suitable gel known to those skilled in the art can be used, such as, for example, gels of acrylamide, agar, dextran, agarose, methylcellulose, guar gum, pullulan, and polyvinylalcohol. In a presently preferred embodiment of this method, crosslinked polyacrylamide gels with a total concentration T>20% (v/w) and a cross-linking concentration C=3% (w/w) are used. It should be noted that the pores of a polyacrylamide gel decrease when T increases provided C≤3%, and that these C-values give transparent gels, independent of the T-values. In contrast, for C-values>5%, the pore size increases when C increases and the gels become white and non-transparent.

A short plug of the gel 19 is introduced into one end of the capillary tube 13 filled with sample solution by pressing the capillary tube into the gel in the glass tube. Preferably, the short plug of the gel 19 is introduced into the first end of the capillary tube 13. The capillary tube 13 should be drawn up slowly to avoid detachment of the gel plug from the end of the capillary tube 13. Upon applying the voltage between the anode 18 and the cathode 17, i.e., upon electrophoresis, the solutes migrate toward the end of the capillary tube containing the short plug of the gel 19, but they cease migrating for stearic reasons when they come into contact with the gel plug 19, thereby concentrating the solution of solutes into very narrow concentrated zones 16. (See, e.g., FIG. 1(B).)

Figure 1C:
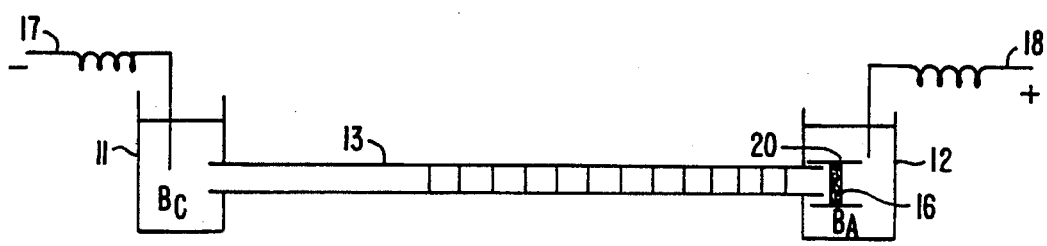

In yet another aspect of the concentration method, step (c) comprises attaching to the first end of the capillary tube 13 a second tube 20 such that upon applying the voltage between the anolyte 12 and the catholyte 11, the solutes exit the first end of the capillary tube 13 and enter the second tube 20 wherein the solutes cease migrating due to an abrupt decrease in field strength and concentrate into very narrow zones 16. (See, e.g., FIG. 1(C).)

In this particular method, a short piece of dialysis tubing 20 is attached to one end of the capillary tube 13 containing the sample solution of solutes to be concentrated. (See, e.g., FIG. 1(C).) Alternatively, the dialysis tubing 20 can be replaced by tubing made of a small-pore gel of polyacrylamide or other suitable gel. Upon applying a voltage between the anode 17 and the cathode 18, the solutes begin to migrate in the direction of the dialysis tubing 20. When the solutes leave the capillary tube 13, the field strength decreases abruptly (i.e., q in Equation I increases) and the migration velocities of the solutes become virtually zero. In this concentration method, the low-molecular weight ions in the sample are removed by diffusion through the pores in the dialysis tubing 20 or, alternatively, the gel. Prior to subsequent electrophoretic analysis, the concentrated sample 16 in the dialysis tubing 20 (or in the gel) is moved hydrodynamically 1–2 mm into the capillary or electrophoresis tube 13 by, for example, raising the fight electrode vessel 12. Alternatively, the capillary or electrophoresis tube 13 can be moved to the left so that the section of the dialysis tubing 20 (or the gel) which contains the concentrated sample zone 16 will be in contact with air.

As an alternative to attaching a short piece of dialysis tubing to the end of the capillary tube, Applicants have now discovered that a dialysis tubing can be prepared and attached directly to an electrophoresis or capillary tube by dipping the tube three or four times into about a 2% to about an 8% nitrocellulose (collodion) solution. (See, e.g., FIG. 4.) In a presently preferred embodiment, a 3% nitrocellulose solution is used. It should be noted that in between the dippings, the ether is allowed to evaporate. Subsequently, the wall of the electrophoresis or capillary tube 13 is then broken manually to create pores 23 in the wall through which the current can pass. The glass pieces 24 are held together by the collodion membrane/tubing 25 formed. In contrast to the above method wherein a short piece of dialysis tubing is attached to one end of the capillary tube, the advantage of this method is that the concentrated zone of solutes never leaves the electrophoresis or capillary tube.

In a further aspect of the method for concentrating a solution of solutes, step (c) comprises attaching to the first end of the capillary tube 13 a second tube 20 and creating a conductivity gradient 22 at the first end of the capillary tube 13 through the use of an anolyte having a high ionic strength such that the conductivity gradient 22 prevents substantially all of the solutes from migrating out of the first end of the capillary tube 13 into the second tube 20. (See, e.g., FIG. 1D)

Figure 1D:
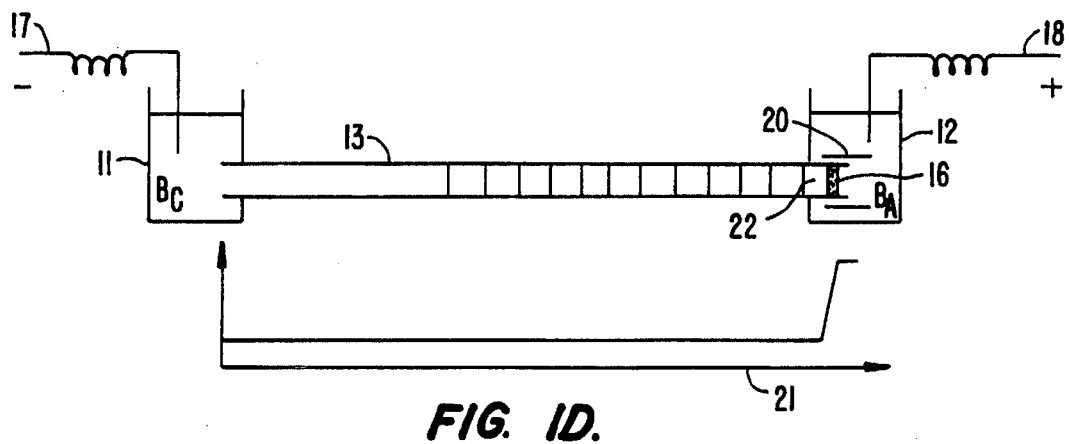

If the right electrode vessel 12 in FIG. 1(D) is filled with a buffer of high ionic strength, the conductivity (i.e., concentration) gradient formed at the anodic end of the capillary tube 13 will prevent substantially all of the sample from migrating into the dialysis tubing 20 (or, alternatively, the gel) and thus, it will cause the sample to concentrate into very narrow zones 16. (The graph in FIG. 1(D) 21 depicts the conductivity gradient 22 formed using this method.) It should be noted that a zone sharpening occurs when the voltage is applied between the anode 18 and the cathode 17 if the buffer in the sample has a conductivity lower than that of the buffer in the electrophoresis or capillary tube 13. Following the concentration of the solution of solutes into narrow concentrated zones, the sample should be moved into the dialysis tubing 20 (or the gel) for removal of salts by dialysis against a dilute buffer in the right electrode vessel 12.

In still a further aspect of the above concentration method, step (c) comprises creating a hydrodynamic counterflow having a force which is equal and opposite to the force of the electrophoretic flow. (See, FIGS. 5(A) and 5(B)). In this concentration method, displacement electrophoresis or zone electrophoresis is carried out in a diluted buffer against a hydrodynamic counterflow. In this method, the counterflow and the electrical field strength are continually adjusted so that the electrophoretic flow has a force equal and opposite to the force of the hydrodynamic counterflow. If this condition is fulfilled, the front of the electrophoretically migrating zone becomes stationary while the rear of the migrating zone continues to migrate until it eventually stacks up against the stationary front of the zone, thereby concentrating the solutes contained therein. The counterflow in the above method can be created in a number of different ways, such as, for example, by having the buffer level in the right electrode vessel a little bit higher than that in the left electrode vessel.

It should be noted that when applied to capillary electrophoresis, the methods described herein permit concentration of a solution of solutes in the same capillary tube as is used for the electrophoretic analysis. Alternatively, however, the sample can be withdrawn from the capillary tube following concentration of the solution of solutes and processed by techniques other than high-performance capillary electrophoresis (HPCE).

In another aspect of the present invention, a method is provided for the off-tube concentration (and desalting) of a solution of solutes. In this concentration method, a syringe containing a small-pore gel, having a cavity in the center of the gel which runs from end to end, is used to concentrate and desalt the sample solution of solutes. In this method, a piston or capillary tube (i.e., fused silica tubing) is inserted into and through the cavity of the gel (See, e.g., FIG. 6). The sample is drawn up or sucked up into the syringe containing the small-pore gel by pulling up on the piston or capillary tube. The sample solution of solutes will occupy the cavity of the gel up to the point where the piston has been withdrawn from the gel.

Once inside the cavity of the gel, the sample solution will be desalted by diffusion. Since the gel contains no ions, the ions present in the sample will diffuse out of the sample and into the gel until an equilibrium in the ion concentration between the sample solution and gel is achieved. In addition to being desalted, the sample will also be concentrated due to the Donnan effect. Since the concentration of water in the sample is higher than in the gel, the water present in the sample will diffuse out of the sample and into the gel. Since the gel has a water concentration which is initially lower than the water concentration of the sample, the gel will expand and absorb water from the sample solution until equilibrium is reached at which point there will be no further movement of water. The diffusion of the water out of the sample and into the gel serves to concentrate the sample solution.

Any suitable gel known to those skilled in the art can be used in this method of the present invention. Such gels include, but are not limited to, the following: gels of acrylamide, agar, dextran, agarose, methylcellulose, guar gum, pullulan, and polyvinylalcohol. In a presently preferred embodiment of this method, crosslinked polyacrylamide gels with a total concentration T of about 10% to about 40% (v/w) and a cross-linking concentration C of about 2% to about 50% (w/w) are used. Particular preferred gels are crosslinked polyacrylamide gels with a total concentration T of about 20% (v/w) and a cross-linking concentration C of about 5% (w/w).

Once the sample solution has been concentrated and desalted, the piston or capillary tube can be moved and the concentrated sample solution can be extracted from the cavity of the gel or, alternatively, the subject to be concentrated. Once the concentrated sample has been withdrawn, it can be subsequently analyzed by high performance capillary electrophoresis (HPCE) or by other methods and techniques known to those skilled in the art. This method has successfully been used to concentrate and desalt a solution of urine, the results of which are shown in FIGS. 7(A) and 7(B). From these results, it was determined that a 20-fold concentration of the sample solution was achieved. The concentrated urine sample was subsequently analyzed by capillary electrophoresis. (See, FIG. 7(B).)

In a further aspect of the present invention, another method is provided for the off-tube concentration (and desalting) of a solution of solutes. In this concentration method, a solution of solutes to be concentrated and desalted is added to a vial test tube or other physical structure to which the semi-dry gel can be attached. This structure can have a variety of forms, such as, for example, a cup, groove, donut or other shape capable of retaining the sample solution, having contained therein a semi-dry small-pore gel. (See, e.g., FIG. 8).) Any suitable gel known to those skilled in the art can be used in this method of the present invention. Such gels include, but are not limited to, the following: gels of acrylamide, agar, dextran, agarose, methylcellulose, guar gum, pullulan, and polyvinylalcohol. In a presently preferred embodiment of this method, crosslinked polyacrylamide gels with a total concentration T of about 10% to about 40% (v/w) and a cross-linking concentration C of about 2% to about 50% (w/w) are used. Particular preferred gels are crosslinked polyacrylamide gels with a total concentration T of about 20% (v/w) and a cross-linking concentration C of about 5% (w/w).

Once the sample solution has been placed inside the vial, the sample solution will be desalted by diffusion of the ions out of the sample and into the gel. Since the gel contains no ions, the ions present in the sample will diffuse out of the sample and into the gel until an equilibrium is achieved between the ion concentration in the sample solution and the semi-dry small-pore gel. In addition to being desalted, the sample will also be concentrated due to the Donnan effect. Since the concentration of water in the sample is higher than in the gel, the water contained in the sample solution will diffuse out of the sample and into the gel. Since the gel has a water concentration which is initially lower than the water concentration of the sample, the gel will readily expand and absorb water from the sample solution. The gel will absorb water from the sample solution until equilibrium is reached at which point there will be no further movement of water. This diffusion of water out of the sample and into the gel serves to successfully concentrate the sample solution.

In yet a further aspect of the present invention, a method for analyzing a solution of solutes is provided, the method comprising: (a) filling a capillary tube with the solution of solutes, the capillary tube having a first end in contact with an anolyte and a second end in contact with a catholyte, the catholyte differing in pH from the anolyte by a pH differential; (b) concentrating the solutes into a concentrated solute zone; (c) mobilizing the concentrated solute zone; and (d) subjecting the mobilized concentrated solute zone to electrophoretic analysis.

In the above method, the solution of solutes can be concentrated in accordance with any of the concentration methods discussed above. These include electrophoresis toward a steep pH gradient; electrophoresis toward a small-pore gel; electrophoresis toward a tube permitting the passage of current but not solutes; electrophoresis toward a gradient in conductivity; and electrophoresis toward a hydrodynamic countercurrent flow. Additionally, the samples can be concentrated using the off-tube concentration and desalting methods set forth above. As such, the discussion pertaining to each of these methods for the concentration of a solution of solutes is fully applicable to the concentration step, i.e., step (b), in the above method for analyzing a solution of solutes.

As with the concentration method of the present invention, the above method can be used to analyze ionic polymers or weak electrolytes, preferably ampholytes (e.g., peptides, proteins and nucleic acids), or compounds which can be transformed into these classes of substances by complex formation.

In one aspect of the above method, step (c) comprises mobilizing the concentrated solute zone by displacement electrophoresis. Following concentration of the sample, buffer $B_A$ in the anode vessel is replaced by a terminating buffer, $B_T$ (such as, for example, 0.03M glycine–NaOH, pH 10), and the polarity of the electrodes is reversed.

With reversed polarity of the electrodes, the anion in the terminating buffer (e.g., glycine) forms a migrating boundary with the anion in the buffer $B_C$ in the electrophoresis tube (e.g., chloride). The requirements for displacement electrophoresis are fulfilled if the anions in the sample have a mobility lower than those of the anions in buffer $B_C$ and higher than those of the anions in the terminating buffer, $B_T$. As such, the anions in the sample migrate quickly until they reach the area containing the leading ions (e.g., chloride ions) and then they drastically slow down. The rapid movement of the sample anions behind the leading ion front and the decreased rate of anion migration as they approach the front, result in the concentration or piling up of the sample anions in a tight disc between the leading ions (e.g., chloride ions) and the terminating ions (e.g., glycinate ions). Therefore, in this mobilization or displacement step, the very narrow concentrated solute zone will move without zone spreading toward the left (i.e., the anode in the mobilization and analysis steps).

If the subsequent electrophoretic analysis, i.e., step (d), is based on zone electrophoresis (and not displacement electrophoresis), the mobilization or displacement step should be interrupted as soon as the concentrated solute zone begins to migrate or move toward the left (or, preferably, somewhat earlier). Otherwise, the onset of the zone electrophoresis step will be delayed giving rise to an unnecessarily long analysis time.

To be useful for the mobilization or displacement of the concentrated solute zone of sample anions (e.g., acidic peptides and proteins), the terminator ion (e.g., glycine, pK 9.8) should, in addition to having a mobility lower than that of the leading ion (e.g., chloride) and those of the sample solutes, have a pK value from about 1 to about 2 units higher than the pK value of the leading buffer cation (e.g., Tris, pK 8.1), and the pH value of the leading buffer (e.g., Tris-HCl, pH 8.5) should be close to the pK-value of its cation. If these requirements are fulfilled, the short plug of terminating ions (e.g., glycine) entering the capillary tube during the brief mobilization step, i.e., step (c), will be titrated to the pH of the electrophoresis buffer after the terminating buffer, $B_T$, has been replaced by the zone electrophoresis buffer and the polarity of the electrodes has been reversed. The terminating ion (e.g., glycine) will thus acquire a small net charge and will, therefore, migrate more slowly than all or most of the sample zones. The titration of the terminating ions (e.g., glycine) is very efficient since upon their migration toward the anode they meet new protons and new buffer cations (e.g., Tris) migrating in the opposite direction.

Additionally, it will be readily apparent to those skilled in the art that for the concentration of basic ampholytes, the theoretical considerations are analogous to those presented above for acidic peptides and proteins. For instance, the different buffers should be designed such that the terminator ion (such as, for example, Bis-Tris, pK 6.7) introduced as a short plug in the mobilization or displacement step, loses most of its positive charge as it meets the leading buffer (e.g., the zone-electrophoresis buffer such as 0.05M EPPS, pH 7.5).

In another aspect of the above method, step (c) comprises mobilizing the concentrated solute zone by creating a steep pH gradient. In this method, the buffer in the right electrode vessel used in the concentration step (i.e., the anolyte) is exchanged for a solution of high pH (such as, for example, 0.1M NaOH) so that upon applying a voltage between the anolyte and the catholyte, the acidic solutes migrate toward the positive pole (i.e., the anode or left electrode vessel in the mobilization and electrophoretic steps). For basic solutes which migrate toward the negative pole (i.e., the cathode), a solution with a low pH is chosen (such as, for example, 1M HCl).

Following the concentration of solutes by electrophoresis toward a steep pH gradient or by zone electrophoresis toward a small-pore gel, the concentrated solute zone can be mobilized by a solution having a high pH. This solution should contain no negatively charged ions other than hydroxyl ions. In a presently preferred embodiment, sodium, potassium or ammonium hydroxides are used. As such, the only ions entering the capillary tube are hydroxyl ions, which have a very high mobility and which, accordingly, change the pH very rapidly at the cathodic end of the capillary tube. This is important when concentration is achieved by electrophoresis toward a steep pH gradient, since the concentrated solute zone will broaden upon reversal of the polarity of the electrodes until the initial pH gradient is demolished (i.e., a pH gradient gives a zone sharpening only when the pH increases in the direction of the current). When a sufficiently large number of hydroxyl ions have entered the capillary tube, a reversed pH gradient is created giving rise to a zone-sharpening. This pH gradient migrates toward the anode with the proteins gathered in a very narrow, concentrated zone (i.e., in a zone having a width of about 0.2 mm). At this stage, which takes only 1–2 min to obtain, the mobilizing high-pH solution is replaced by the electrophoresis buffer (i.e., the same buffer that is used in both the anode vessel and in the capillary tube). The plug of hydroxyl ions continues to migrate toward the anode, but its concentration decreases as it meets and reacts with the buffering cations in the capillary tube (e.g., Tris ions which are continuously fed into the capillary tube from the anode vessel). It should be noted that if it is essential to minimize the analysis time, the cathode vessel can be filled with the electrophoresis buffer somewhat before a complete zone-sharpening (i.e., stacking) has been achieved since the large number of hydroxyl ions in the capillary tube at its cathodic end will continue to make the pH-gradient still narrower at the same time as the buffer anions (e.g., chloride) migrate into the capillary tube to destack the concentrated sample constituents.

Equation (VII), which corresponds to Equation (IV), gives the number of hydroxyl ions, $N_{OH-}$, that enter the capillary per time unit:

$$N_{OH-} = \frac{I \times U_{OH-} \times n_{OH-}}{\kappa} \quad \text{(VII)}$$

Using the same reasoning as was used for Equation (IV), i.e., $N_+$, one can show the importance of choosing an appropriate value of $\kappa$, i.e., the conductivity, to increase rapidly the pH at the cathodic end of the capillary tube and, thus, demolish the initial, zone-broadening pH gradient to create a new, reversed, zone-sharpening pH gradient. It has been determined that 0.1M sodium hydroxide is a suitable mobilizing solution independently of which buffer is in the capillary tube. Mobilization by 0.1M sodium hydroxide requires no pre-experiments to establish optimum conditions for each new type of electrophoresis buffer and, thus, it is very simple to carry out. Further, the excess concentration of the hydroxyl ions in the capillary are quickly reduced by the buffering ions in the electrophoresis buffer. Therefore, and also because the solutes will start migrating as soon as the pH is above their pI-values, the solutes will not be located in an area of extremely high pH and, thus, the risk of denaturation is negligible, particularly since the mobilization and, thereby, the possible exposure to elevated pH, has a duration of only about 1–2 min.

It will be readily apparent to those skilled in the art that analogous methods can be used for mobilization at low pH. In a presently preferred method of mobilizing a concentrated solute zone at low pH, 1M HCl is used. Concentration of proteins and peptides can also be performed with a pH gradient created with carrier ampholytes in the same way as is done in conventional isoelectric focusing. However, it has been discovered that the high buffering capacity of these ampholytes makes it difficult to rapidly demolish the pH gradient. Mobilization, therefore, takes place under broadening of the narrow, concentrated solute zone.

In another aspect of the above method, step (c) comprises mobilizing said concentrated solute zone by on-tube dialysis against a dilute buffer. In this method, the concentration of the solution of solutes is achieved with the aid of a dialysis tubing or gel attached to one end of the capillary tube, e.g., the first end of the capillary tube. (See, e.g., FIGS. 1(C) and 1(D)). The solution in the right electrode vessel is exchanged for a buffer with a concentration which is 5–15 fold lower than that in the capillary. Following dialysis for several minutes, the concentrated zone is moved 1–3 mm into the capillary tube by, for example, raising the right electrode vessel. Alternatively, the capillary tube can be moved toward the left so that the section of the dialysis tubing (or, alternatively, the gel) which contains the concentrated dialyzed sample zone will be in contact with air instead of with buffer.

In another aspect of the above method, step (d) comprises subjecting said mobilized concentrated solute zone to displacement electrophoresis. This electrophoretic method is preferably used following mobilization of the concentrated solute zone by displacement electrophoresis. If the concentrated solute zone is mobilized by displacement electrophoresis, the mobilization step is not interrupted, but allowed to proceed until all the solutes have passed the detector. If this electrophoretic method is to be performed following any of the other mobilization methods, it is performed in accordance with conventional methods and procedures known to those skilled in the art.

In yet another aspect of the above method, step (d) comprises subjecting the mobilized concentrated solute zone to zone electrophoresis. When the concentrated solute zone, mobilized by displacement electrophoresis or by a steep pH gradient, is to be subjected to zone electrophoresis, the solution in the right electrode vessel is exchanged for a buffer of the same composition as that in both the capillary tube and the left electrode vessel. Zone electrophoresis is performed in accordance with conventional procedures known to those skilled in the art.

The following examples are offered for illustrative purposes only, and are intended neither to define or limit the invention in any manner.

EXAMPLE I

A. Concentration of Proteins by Zone Electrophoresis Toward a Steep pH Gradient (Isoelectric Focusing) and Mobilization by Displacement Electrophoresis The sample consisted of 20 µg of each of the proteins phycoerythrin, bovine serum albumin, human hemoglobin, carbonic anhydrase and human transferrin, dissolved in 1 mL of 0.01M Tris-HCl, pH 8.5. This buffer was also used as the catholyte in the concentration step. A 0.5M Tris-HCl solution, pH 2.5 served as the anolyte in the concentration step.

The capillary was fused silica tubing of total length 130 mm and effective length 115 mm. The internal diameter of the tubing was 0.05 mm. The capillary tube was filled with the sample solution. A voltage of 1500 V (0.8 µA) was applied during 12 min in order to concentrate the proteins into a narrow zone in the pH gradient. The polarity of the electrodes was reversed following an exchange of the 0.5M Tris-HCl solution, pH 2.5, for 0.03M glycine-NaOH, pH 10.0. At a voltage of 1500 V for 2.5 min, a sharp zone was obtained by displacement electrophoresis (chloride was the leading ion and glycine the terminating ion). The glycine-NaOH buffer was subsequently replaced by 0.01M Tris-HCl, pH 8.5, and an analysis of the sample by zone electrophoresis was performed at 3,000 V, corresponding to 1.6 µA. The electropherogram obtained is presented in FIG. 2B. The detection was made at 220 nm. It should be noted that without the above displacement step, a visual inspection of the experiment in a transparent glass tube indicated that the starting zone in this zone electrophoresis became blurred.

In conjunction with the above experiment, a control experiment was performed without concentrating the sample and with a starting zone as wide as 3–4 mm with the hope of detecting at least the main peaks (FIG. 2A). A comparison between FIGS. 2A and 2B demonstrates the efficiency and benefit of the concentration technique. The width of the concentrated starting zone in the zone electrophoresis step was about 0.2 mm (visual observation). From the length of the capillary and this zone width, it can be concluded that approximately a 500-fold concentration of the sample was obtained. The recovery of the sample mixture was difficult to determine quantitatively because of the small amount of protein used to carry out the experiment. It is estimated, however, that the recovery of the sample should be close to 100% judging from the fact that none of the strongly colored phycoerythrin was observed after a completed run in a parallel experiment in a transparent glass tube.

The above buffer system is designed for acidic peptides and proteins and other ampholytes. For basic ampholytes, we have used the following buffers:

(a) The Concentration Step (isoelectric focusing): 0.05M N-hydroxyethylpiperazine propane sulfonic acid (EPPS), pH 7.5, in the left electrode vessel (i.e., the anolyte) and in the capillary; 0.25M EPPS pH, 11.0, in the right electrode vessel (i.e., the catholyte). EPPS is titrated to the desired pH with sodium hydroxide.

(b) The Displacement Step: 0.05M EPPS, pH 7.5, in the left electrode vessel (i.e., now the catholyte) and in the capillary; 0.1M Bis-Tris (titrated to pH 2.0 with HCl) in the right electrode vessel (i.e., now the anolyte).

(c) The Free Zone Electrophoresis Step: 0.05M EPPS, pH 7.5, in both electrode vessels and in the capillary. It should be noted that the polarity in the electrophoretic step is the same as in Mobilization Step.

B. Concentration of Proteins By Zone Electrophoresis Toward a Small-Pore Polyacrylamide Gel and Mobilization By Displacement Electrophoresis Followed By Zone Electrophoresis The capillary was fused silica tubing of total length 130 mm and effective length 115 mm. The internal diameter of the tubing was 0.05 min. The capillary tube was filled with a solution of the same proteins as were used in the previous experiment, i.e., phycoerythrin, bovine serum albumin, human hemoglobin, carbonic anhydrase and human transferrin. They were dissolved in the same buffer (0.01M Tris-HCl, pH 8.5) to the same concentrations (20 µg/mL). This buffer was also employed as the catholyte in steps I and III. The catholyte in step II (i.e., the terminating solution) was 0.03M diaminopimelic acid, titrated to pH 9.2 with Tris.

With a polyacrylamide gel of the composition T=60% (v/w) and C=3% (w/w) at the anodic end of the capillary tube, the concentration toward the gel plug was finished in 10 min at 2000 V. In this concentration step, the anolyte was 0.01M Tris-HCl, pH 8.5. The mobilization by displacement electrophoresis of the very narrow, concentrated protein zone took place at 2000 V for 1.5 min following a reversal of the polarity of the electrodes. This displacement electrophoresis step was introduced to avoid a broad starting zone in the subsequent zone electrophoresis which was performed at 3000 V with the diaminopimelic acid-Tris buffer in the cathode vessel exchanged for 0.01M Tris-HCl, pH 8.5 (FIG. 3B).

The experiment was repeated with the difference that the analysis was performed without prior concentration of the sample. The width of the starting zone was 3–4 mm. The 0.01M Tris HCl buffer (pH 8.5) was used both in the capillary and in the anode and cathode vessels. The striking difference between the electropherogram obtained in FIG. 3A and that obtained in FIG. 3B shows the importance of having access to a method for in-tube concentration of dilute protein solutions. The width of the concentrated starting zone in the zone electrophoresis step was about 0.2 mm (visual observation). From the length of the capillary and the observed zone width, it can be concluded that approximately a 500-fold concentration of the sample was obtained.

The foregoing is offered primarily for purposes of illustration. It will be readily apparent to those skilled in the art that modifications and variations of the materials and/or procedures described herein may be introduced with successful results without departing from the spirit and scope of the invention.

What is claimed is:

1. A method for analyzing a solution of solutes, said method comprising, sequentially (a) filling a capillary tube with said solution of solutes, said capillary tube having a first end in contact with an anolyte and a second end in contact with a catholyte, said catholyte differing in pH from said anolyte by a pH differential;

(b) concentrating said solutes into a concentrated solute zone;

(c) mobilizing said concentrated solute zone; and (d) subjecting said mobilized concentrated solute zone to electrophoretic analysis.

2. A method in accordance with claim 1 wherein step (b) comprises applying a voltage between said anolyte and said catholyte of sufficient intensity to cause said solutes to migrate electrophoretically to said first end of said capillary tube, while imposing a means of concentrating said solutes on said first end of said capillary tube.

3. A method in accordance with claim 2 wherein said means of concentrating said solutes comprises creating a non-buffering steep pH gradient at said first end of said capillary tube through the use of an anolyte having a pH which is substantially different from said pH of said catholyte and said pH of said solution of solutes.

\* \* \* \* \*